(12) United States Patent
Storey et al.

(10) Patent No.: US 8,066,854 B2
(45) Date of Patent: Nov. 29, 2011

(54) ANTIMICROBIAL COATING METHODS

(75) Inventors: Daniel M. Storey, Longmont, CO (US); Deidre Sewell, Fort Collins, CO (US); Terrence S. McGrath, Longmont, CO (US); John H. Petersen, Longmont, CO (US)

(73) Assignee: Metascape LLC, Maple Grove, MN (US)

( * ) Notice: Subject to any disclaimer, the term of this patent is extended or adjusted under 35 U.S.C. 154(b) by 1384 days.

(21) Appl. No.: 11/406,607

(22) Filed: Apr. 19, 2006

(65) Prior Publication Data

US 2006/0198903 A1    Sep. 7, 2006

Related U.S. Application Data

(63) Continuation-in-part of application No. 10/741,015, filed on Dec. 18, 2003, now abandoned.

(60) Provisional application No. 60/434,784, filed on Dec. 18, 2002.

(51) Int. Cl.
*C23C 14/32* (2006.01)

(52) U.S. Cl. .............. 204/192.38; 204/298.41

(58) Field of Classification Search ............ 204/298.41, 204/192.38
See application file for complete search history.

(56) References Cited

U.S. PATENT DOCUMENTS

| | | |
|---|---|---|
| 3,953,239 A | 4/1976 | Anderson |
| 4,219,125 A | 8/1980 | Wiltshire et al. |
| 4,322,276 A | 3/1982 | Meckel et al. |
| 4,411,648 A | 10/1983 | Davis et al. |
| 4,492,845 A | 1/1985 | Kljuchko et al. |
| 4,592,920 A | 6/1986 | Murtfeldt |
| 4,828,832 A | 5/1989 | De Cuellar et al. |
| 4,876,423 A | 10/1989 | Tighe et al. |
| 4,886,505 A | 12/1989 | Haynes et al. |
| 4,913,782 A | 4/1990 | Seiger |
| 4,930,211 A | 6/1990 | Gaudino |
| 4,957,771 A | 9/1990 | Enloe |
| 5,098,582 A | 3/1992 | Antelman |
| 5,269,898 A | 12/1993 | Welty |
| 5,277,714 A | 1/1994 | Tamagaki |
| 5,320,908 A | 6/1994 | Sodervall et al. |
| 5,336,499 A | 8/1994 | Antelman |
| 5,342,283 A | 8/1994 | Good |

(Continued)

FOREIGN PATENT DOCUMENTS

DE    2044165    3/1971

(Continued)

OTHER PUBLICATIONS

Antimicrobial Biodegradable Coating to Reduce Catheter Infection Risk, *News from BPC*, 2003, (www.rpsgb.org.uf/events/bpc.htm).

(Continued)

*Primary Examiner* — Keith Hendricks
*Assistant Examiner* — Jason M Berman
(74) *Attorney, Agent, or Firm* — Saliwanchik, Lloyd & Eisenschenk

(57) ABSTRACT

The invention is directed to efficient methods for depositing highly adherent anti-microbial materials onto a wide range of surfaces. A controlled cathodic arc process is described, which results in enhanced adhesion of silver oxide to polymers and other surfaces, such as surfaces of medical devices. Deposition of anti-microbial materials directly onto the substrates is possible in a cost-effective manner that maintains high anti-microbial activity over several weeks when the coated devices are employed in vivo.

11 Claims, 2 Drawing Sheets

U.S. PATENT DOCUMENTS

| | | | |
|---|---|---|---|
| 5,405,718 A | 4/1995 | Hashemi | |
| 5,454,886 A | 10/1995 | Burrell et al. | |
| 5,753,251 A | 5/1998 | Burrell et al. | |
| 5,770,255 A | 6/1998 | Burrell et al. | |
| 5,785,972 A | 7/1998 | Tyler | |
| 5,824,267 A | 10/1998 | Kawasumi et al. | |
| 5,830,526 A | 11/1998 | Wilson et al. | |
| 5,837,275 A | 11/1998 | Burrell et al. | |
| 5,958,440 A | 9/1999 | Burrell et al. | |
| 5,985,308 A | 11/1999 | Burrell et al. | |
| 6,080,490 A | 6/2000 | Burrell et al. | |
| 6,103,074 A * | 8/2000 | Khominich | 204/192.38 |
| 6,174,329 B1 | 1/2001 | Callol et al. | |
| 6,238,686 B1 | 5/2001 | Burrell et al. | |
| 6,239,048 B1 | 5/2001 | Wilson et al. | |
| 6,258,385 B1 | 7/2001 | Antelman | |
| 6,333,093 B1 | 12/2001 | Burrell et al. | |
| 6,346,327 B1 | 2/2002 | Mokerji | |
| 6,365,220 B1 | 4/2002 | Burrell et al. | |
| 6,413,387 B1 | 7/2002 | Shi et al. | |
| 6,511,585 B1 | 1/2003 | Shi et al. | |
| 6,530,951 B1 | 3/2003 | Bates et al. | |
| 6,533,908 B1 | 3/2003 | Meyer et al. | |
| 6,579,428 B2 | 6/2003 | Takigawa et al. | |
| 6,602,390 B1 * | 8/2003 | Brandle et al. | 204/298.41 |
| 6,673,385 B1 | 1/2004 | Ding et al. | |
| 6,702,931 B2 | 3/2004 | Brandle et al. | |
| 6,709,693 B1 | 3/2004 | Dinkelborg et al. | |
| 6,861,105 B2 | 3/2005 | Veersamy | |
| 6,866,753 B2 | 3/2005 | Miyake | |
| 6,875,326 B2 | 4/2005 | Inaba et al. | |
| 6,918,927 B2 | 7/2005 | Bates et al. | |
| 6,936,145 B2 | 8/2005 | Sunthankar et al. | |
| 6,951,630 B2 | 10/2005 | Neuberger | |
| 7,008,667 B2 | 3/2006 | Chudzik et al. | |
| 7,250,196 B1 | 7/2007 | Kidd et al. | |
| 7,255,881 B2 | 8/2007 | Gillis et al. | |
| 2003/0194433 A1 | 10/2003 | Hei et al. | |
| 2004/0038068 A1 | 2/2004 | Finch et al. | |
| 2004/0054399 A1 | 3/2004 | Roth | |
| 2004/0134770 A1 * | 7/2004 | Petersen | 204/192.38 |
| 2004/0185182 A1 | 9/2004 | Lipkin et al. | |
| 2005/0182152 A1 | 8/2005 | Nonninger et al. | |
| 2005/0187466 A1 | 8/2005 | Glocker et al. | |
| 2005/0226931 A1 | 10/2005 | Gibbins et al. | |
| 2005/0271743 A1 | 12/2005 | Burrell et al. | |
| 2005/0288773 A1 | 12/2005 | Glocker et al. | |

FOREIGN PATENT DOCUMENTS

| | | |
|---|---|---|
| DE | 19600993 | 8/1996 |
| WO | WO 03/044240 A1 | 5/2003 |
| WO | WO 2004/059027 | 7/2004 |

OTHER PUBLICATIONS

Dorau, B., et al., An Investigation into the Potential of Ionic Silver as a Wood Preservative, Woodframe, Housing, Durability, and Disaster Issues, pp. 133-145.

Gorman, S. et al., Antimicrobial Biomaterials for Medical Devices, *Business Briefing: Medical Device Manufacturing & Technology*, 2002, pp. 1-4.

Kumar, R.S. et al., Antioxidant and antimicrobial activities of *Bauhinia racemosa* L. stem bark, *Brazilian Journal of Medical and Biological Research*, 2005, pp. 1015-1024, vol. 38, No. 7.

Malik, Zvi., et al., Antimicrobial and antiviral activity of porphyrin photosensitization, Life Sciences Department, Bar-Ilan University, Israel. (http://www.lumacare.com/paper14.htm. pp. 1-5.).

McMillan, J.A., Higher Oxidation States of Silver, 1961, pp. 65-80, Argonne National Laboratory, Argonne, Illinois.

Pyrek, Kelly M., Battling Biofilm: Surface Science, Antimicrobials Help Combat Medical Device Related Infections, *Infection Control Today*, (www.infectioncontroltoday.com/articles/291feat3.html).

Zhao, L., Singlet Oxygen, 2001, pp. 1-10Free Radical and Radiation Biology Graduate Program, Department of Radiology, The University of Iowa.

Kirk-Othmer Encyclopedia of Chemical Technology, 4$^{th}$ Edition, vol. 23, John Wiley and Sons, 1997, pp. 1040-1056.

\* cited by examiner

ANTIMICROBIAL COATING METHODS

This application is a continuation-in-part application of U.S. patent application Ser. No. 10/741,015 filed Dec. 18, 2003 now abandoned which claims benefit of U.S. Provisional Application Ser. No. 60/434,784, filed Dec. 18, 2002, the disclosure of which is incorporated by reference.

FIELD OF THE INVENTION

The invention relates to cathodic arc ion plasma deposition methods for preparing modified metal coatings useful for forming an anti-microbial surface on devices and materials used in medical applications. In particular, the invention relates to a process for depositing silver (Ag), and other anti-microbial metals, or combinations thereof under highly controlled conditions to form antimicrobial coatings that have improved adhesion and maintain activity over extended periods of time.

BACKGROUND

The germicidal properties of metals such as silver, zinc, niobium, tantalum, hafnium, zirconium, titanium, chromium, nickel, copper, platinum and gold are well documented. Of these metals, silver, in the form of ions or compounds, is probably the best known and most widely used anti-microbial metal. Elemental silver has some anti-microbial benefit, but is generally too unreactive for most anti-microbial applications. An oxidized form of silver is considered to be more active as an anti-microbial as indicated by the observation that painting and inking of silver oxides leads to a decrease in their reactivity and solubility.

Attempts have been made to improve the reactivity of silver through the use of silver oxides and combinations of silver with other materials using accepted methods of solution-based chemistry. U.S. Pat. No. 4,828,832 describes the use of metallic silver salt solutions such as aqueous silver nitrate in combination with an oxidizing agent, such as benzoyl peroxide, to treat skin infections.

U.S. Pat. No. 5,824,267 discloses imbedding the surface of a plastic article with silver metal particles and ceramic or base metal particles to impart antibacterial properties to the plastic article. The extremely fine silver metal particles are obtained by chemical deposition from an aqueous silver salt solution.

Although solution methods of generating silver particles are able to provide anti-microbially active silver, there is little control over the structure of the resulting silver particles, so that these methods are limited in their applications. Moreover, some ionic species, such as aqueous silver nitrate, are too reactive for most applications because of the potential for skin irritation and must therefore be carefully monitored and controlled. Another problem with solution-based chemistry is the development of stable combinations without generating harmful byproducts. Silver ions bound in solutions of pastes, paints, polymers or gels tend to have a short shelf life, in part because of the side reactions with various constituents that can occur in water-based solutions.

There is a distinct need for anti-microbial surfaces that are capable of generating a sustained release of anti-microbial metal ions. The ability of a surface to generate a sustained release of anti-microbial ions would be particularly useful in surgical and wound dressings and bandages, surgical sutures, catheters and other medical devices, implants, prosthetics, dental applications and tissue regeneration. Other devices that would also benefit from a sustained release of anti-microbial materials include medical tools and surfaces, restaurant surfaces, face masks, clothing, door knobs and other fixtures, swimming pools, hot tubs, drinking water filters, cooling systems, porous hydrophilic materials, humidifiers and air handling systems.

A method for generating a sustained release of metallic ions is described in U.S. Pat. No. 4,886,505. According to the method, a device is coated with a first metal, such as silver, and a second metal, such as platinum, which is connected to the first metal through a switch. The presence of the silver and platinum metals in the presence of body fluids results in a galvanic action which is intended to release or liberate silver ions. The release of ions is controlled by the switch, which is operated external to the device.

The technique of applying a current to a silver-coated wound dressing or medical device is also the subject matter of U.S. Pat. Nos. 4,219,125 and 4,411,648. Although the use of external switch controls or an external electric current can enhance the rate of metal ion release, such external controls or currents may not be practical for a variety of applications.

U.S. Pat. No. 6,365,220 describes a process for producing an anti-microbial surface that provides a sustained a release of anti-microbial ions without the need for an external electric current to maintain the release. According to the disclosure, multiple layers of metallic thin films are deposited on a substrate using a sputtering or evaporation processes. By using different metal combinations for the different layers, and employing etching techniques to roughen or texture the surface of the layers, multiple microlayer interfaces can be generated. The multiple interfaces, when exposed to body fluids, provide for release of ions by galvanic and non-galvanic action.

U.S. Pat. No. 5,837,275 also discloses anti-microbial coatings that provide a sustained release of anti-microbial ions. Coatings are prepared by a sputter technique using specific deposition parameters. The coatings are described as metal films exhibiting "atomic disorder" which is claimed to be required for sustained release of metallic ions.

Single ordered crystals of tetrasilver tetroxide ($Ag_4O_4$) are claimed to be useful as an anti-microbial in treating skin diseases (U.S. Pat. No. 6,258,385.) Such a composition, however, is not practical for other than topical use, and its ability to provide a sustained release of anti-microbial materials over a long period of time (i.e. several days) without reapplication, has not been demonstrated.

Deposition of anti-microbial materials is commonly limited to one of three distinct methods for producing silver and silver oxide coatings. Each of these methods has serious disadvantages and none have been developed to efficiently produce highly adherent, evenly distributed anti-microbial films on surfaces of medical devices and instruments. Commonly used state of the art processes, such as sputtering, dip and Ion Beam Assisted Deposition, produce coatings with limited adhesion to flexible substrates or elastic devices. Additional layers to increase adhesion are sometimes necessary at a significant cost in processing time.

Deposition of metal materials on a substrate by cathodic arc in a vacuum is known in the art. In contrast to other plasma vapor deposition methods, ion plasma deposition (IPD) can produce dense multi-component coatings of high purity as described in U.S. Patent Application Pub. No. 2004/0185182. However conventional cathodic arc deposition methods suffer from certain disadvantages. A waste of expensive material can occur due to inefficient use of the target material and the lack of particle control. The lack of control over the material being deposited can result in the formation of particles of varying sizes, which leads to the deposition of non-uniform coatings. Typically the cathodic arc processes also require the substrate surface to be heated to very high temperatures, which can damage the substrate material and severely restrict the choice of substrates.

BRIEF SUMMARY OF THE INVENTION

The present invention addresses the continuing need for anti-microbial materials that will adhere to any surface, have controlled release rates and longevity, and are nontoxic in a desired application. Anti-microbial coatings with these characteristics can be deposited on a wide range of substrate surfaces using the novel cathodic arc IPD deposition process, herein described.

It is an object of the present invention to provide a method of depositing anti-microbial materials onto a substrate by using an ionic plasma deposition process to form discrete layers of anti-microbial particles.

A further object of the invention is to provide a method for producing anti-microbial surfaces on any finished product, thus eliminating the need to employ complex chemistry, pasting, printing and bonding technologies.

Another object of the invention is to provide an anti-microbial surface that provides a sustained release of an anti-microbial agent in vivo at therapeutically effective levels for extended periods of time.

Another object of the invention is to provide an anti-microbial surface by impregnating or depositing dispersed metals and/or metal/metal oxides of one or more elements into a substrate for the sustained release of metal ions.

Accordingly, in particularly preferred embodiments, the present invention provides the deposition, impregnation or layering of silver or other metal ions bound into solid state structures of nano-, pico-, and micro-sized crystalline metal and metal oxide compounds which can be designed as combinations of mono-, di-, and polyvalent oxides dispersed into or onto a surface. The silver ions will then be released by contact with pathogens due to enzyme activity or released by the addition of water or contact with body fluids.

The disclosed process is useful for the manufacture of a wide variety of devices which require a controlled composition, but is particularly useful in the manufacture of small to very large area rolls, such as bandages, or individual parts, such as catheters, stems or implants, that require a germicidal, bactericidal, biocidal or anti-microbial surface. The process results in the control of the amount, particle size and energy of ionized material to be combined with ionized oxygen or other gases, and is applicable to a wide range of monovalent, divalent, and polyvalent oxides and nitrides and combinations of layers.

The process can be used to make anti-microbial products or to surface treat existing products and raw materials. The process can be used concurrently to create small scale energy devices to enhance anti-microbial activity or to power other nano-technology devices; for example, silver oxide batteries to power micropumps, implants, galvanic surfaces and other devices needing power.

Accordingly, one aspect of the invention is to provide a process for depositing an anti-microbial surface on a substrate which comprises the steps of placing a cathode target comprising a potential anti-microbial metal into an evacuated chamber and powering the cathode to generate an arc at the cathode which ionizes the cathode metal into a plasma of ionized particles; introducing a reactive gas, such as oxygen, into the vacuum chamber such that the gas reacts with the ionized plasma particles, and controlling deposition of the plasma particles on the substrate by moving the substrate closer or further from the target in a controlled manner during the deposition process.

Further control of the deposition process may be achieved by an arc control means whereby the power supply to the cathode is adjusted to alter the speed of arc production.

An additional aspect of the invention is to provide on a substrate, an anti-microbial surface comprising a dispersion of metal oxide particles, wherein the metal is selected from the group consisting of silver, nickel, zinc, copper, gold, platinum, niobium, tantalum, hafnium, zirconium, titanium, chromium, and combinations thereof.

The present invention relates to a process of depositing anti-microbial materials onto a selected substrate material. The substrate can be of any material, such as metal, ceramic, plastic, glass, flexible sheets, porous papers, ceramics or combinations thereof. Although the substrate can comprise any of a number of devices, medical devices are particularly preferred. Such medical devices include catheters, implants, stents, tracheal tubes, orthopedic pins, shunts, drains, prosthetic devices, dental implants, dressings and wound closures. However, it should be understood that the invention is not limited to such devices and may extend to other devices useful in the medical field, such as face masks, clothing, surgical tools and surfaces.

There are two important factors regarding implant infection: the introduction of bacteria during implant surgery; and, transdermal openings following surgery. Transdermal devices are a prime location for infections. As the device separates from the skin, a fissure forms between the skin and device, allowing bacterial contamination.

This invention, in further aspects, is related to improved and more economical methods for providing tuned anti-microbial surfaces or other components on medical devices for use in the human body as well as in veterinary and other applications.

Anti-microbial material can be any solid material or combination of materials having anti-microbial properties. Preferred materials are metals having potential anti-microbial properties and which are biocompatible (i.e., not damaging in the intended environment). Such metals include silver, zinc, niobium, tantalum, hafnium, zirconium, titanium, chromium, nickel, copper, platinum and gold (also referred to herein as "anti-microbial metals"). The term "potential anti-microbial properties" is meant to recognize the fact that these metals, in their elemental state, are typically too un-reactive to act as effective anti-microbials. However, there is a much stronger anti-microbial effect when the metals are ionized. Thus, the anti-microbial metals have potential anti-microbial properties, which are realized upon ionization of the metals. When ionized, the anti-microbial metals can also be combined with various reactive gases, for example, nitrogen or oxygen to form compounds of nitrides, oxides, and/or combinations thereof.

DEFINITIONS

Ionic Plasma Deposition (IPD) is a method of creating highly energized plasma by using a cathodic arc discharge on a target material.

Cathodic arc, also known as a vacuum arc, is a device for creating a plasma from solid metal. An arc is struck on the metal, and the arc's high power density vaporizes and ionizes the metal, creating a plasma which sustains the arc. A vacuum arc is different from a high-pressure arc because the metal vapor itself is ionized, rather than an ambient gas Macros or macro particles are particles larger than a single ion; nano (or small) particles are particles about 100 nanometers in size; medium macro particles are 100 nanometers to about 1 micron; large macro particles are particles larger than 1 micron.

Coulomb explosion occurs when a sufficiently intense power source disrupts a group of atoms such as a gas cluster, object, or target so that the electric field of the power source drives some or all of the electrons off the atoms. Without electrons, the group of ions explodes due to the Coulombic repulsion of the positive charges.

Plasma vapor deposition (PVD) is a thin film deposition process in the gas phase in which source material is physically transferred in the vacuum to the substrate without any chemical reaction involved. This type of deposition includes thermal evaporation electron-beam deposition and sputtering deposition. The IPD process is a subtype of physical vapor deposition.

The term "medical device" as used herein is intended to extend broadly to all devices used in the medical field, including stents, catheters, various implants and the like regardless of the material from which it is fabricated. References herein to medical devices and other medical references are understood to also include veterinary devices and applications.

The term "potential anti-microbial properties" is meant to recognize the fact that some metals, in their elemental state, are typically too unreactive to act as effective anti-microbials, but may, however, exhibit a much stronger anti-microbial effect when ionized. Thus, the anti-microbial metals have potential anti-microbial properties, which in many cases are realized upon ionization of the metals. When ionized, the anti-microbial metals can also be combined with various reactive gases, for example, nitrogen, or oxygen to form compounds of nitrides or oxides, and combinations thereof.

"Multivalent" as used herein refers to one or more valence states and should be understood to refer to the charge on an ion or the charge that may be assigned to a particular ion based on its electronic state.

Silver oxide, unless otherwise indicated, is defined as the singlet form of silver oxide (AgO).

The term "about" as used herein is intended to indicate that a particular number is not necessarily exact but may be higher or lower as determined by the particular procedure or method used.

PEEK—poly ether ether ketone
PTFE—poly tetra fluoro ethylene
EPTFE—expanded poly tetra fluoro ethylene
UHMWPE is ultra high—molecular weight polyethylene
It is understood that "a" as used to define the claims is not necessarily limited to a single species.

DETAILED DESCRIPTION OF THE INVENTION

Figure 1:
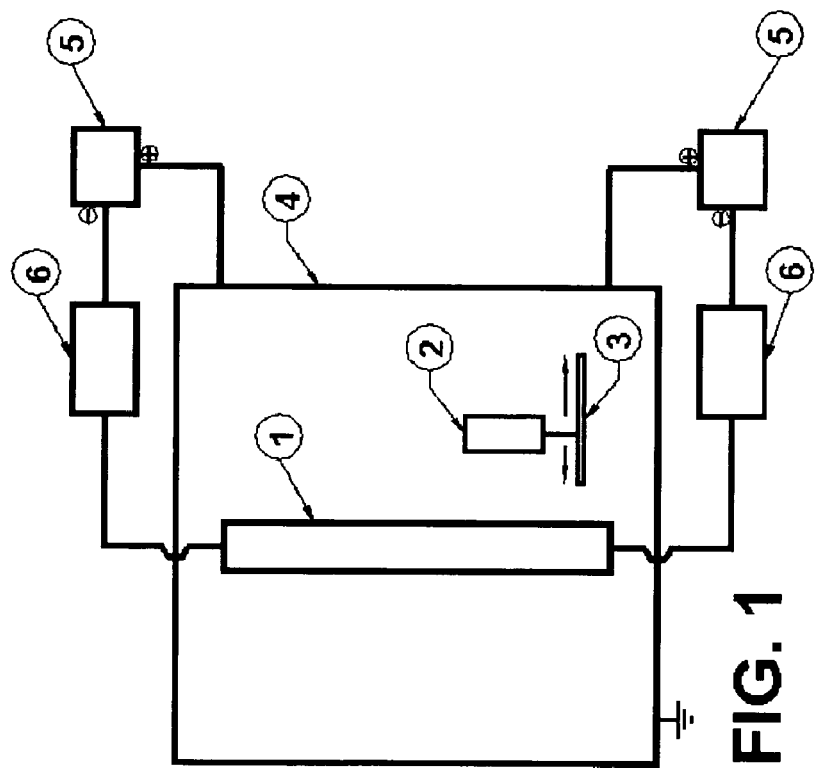
FIG. 1 is a sketch of an IPD apparatus. 1. Target material, 2. Substrate being coated, 3. Mechanism for moving the substrate closer or further away from the target, 4. Vacuum chamber, and 5. Power supply for the target.

The present invention provides a number of advantages over other state of the art anti-microbial coatings and processes for depositing anti-microbial coatings, including controllable release, embedding the coating into the substrate, lower run temperatures for certain materials, significantly improved throughput in processing efficiency compared with conventional cathodic arc processes, scalability, and application to a wide range of substrate materials.

Additionally, superior coatings unavailable using conventional IPD methods have been obtained, including silver oxide, copper oxide and hafnium nitride coatings. These materials have a higher anti-microbial activity at comparable thicknesses compared to more expensive processes, such as those outlined in U.S. Pat. No. 5,454,886, incorporated herein by reference. Thus, thinner coatings and shorter processing time, can be achieved with the same anti-microbial results by employing the new IPD-based methods. Higher throughput is possible, which can result in production cost savings and is a very significant advantage, especially for the medical industry.

A factor contributing to the superiority of films obtained using the disclosed process is the discovery that the new IPD process produces an increase, rather than a decrease, in macro particle deposition, which in fact improves film quality. The predominant trend for one skilled in the use of traditional cathodic arc deposition processes has for years been to reduce macro particles deposited in order to produce cleaner and more uniform films. Conventional wisdom in the industry has been that macro-particles in general are deleterious to the quality of deposited films.

The present invention relates to a process of depositing anti-microbial materials onto a selected substrate material. The substrate can be of any material, such as metal, ceramic, plastic, glass, flexible sheets, porous papers, ceramics or combinations thereof. Although the substrate can be any of a number of devices, medical devices are particularly preferred, including catheters, implants, stents, tracheal tubes, orthopedic pins, shunts, drains, prosthetic devices, dental implants, dressings and wound closures. However, it should be understood that the invention is not limited to such devices and may extend to other devices useful in the medical field, such as face masks, clothing, surgical tools and surfaces.

There are two important factors regarding implant infection: the introduction of bacteria during implant surgery; and, transdermal openings following surgery. Transdermal devices are a prime location for infections. As the device separates from the skin, a fissure forms between the skin and device, allowing bacterial contamination.

The present invention, therefore, is related to improved and more economical methods for providing anti-microbial surfaces or other components on medical devices for use in the human body as well as in veterinary and other applications. The anti-microbial material can be any solid material or combination of materials having anti-microbial properties. Preferred materials are metals having potential anti-microbial properties and which are biocompatible (i.e., not damaging in the intended environment). Such metals include silver, zinc, niobium, tantalum, hafnium, zirconium, titanium, chromium, nickel, copper, platinum and gold (also referred to herein as "anti-microbial metals"). In accordance with the present invention, anti-microbial metals are deposited onto or into the surface of a substrate by ionizing, in a vacuum, a cathode of a target metal into a plasma of particulate constituents. Ionic plasma deposition devices, such as those described in International Patent Application publication WO 03-044240, the contents of which are herein incorporated by reference, can be modified in accordance with the invention and used to carry out the controlled deposition of the anti-microbial materials in accordance with the described methods.

A factor contributing to the superiority of films obtained using the new IPD process is the discovery that an increase, rather than a decrease, in macro particle deposition in fact improves film quality. The predominant trend for one skilled in the use of cathodic arc deposition processes has for years been to reduce the number of macro particles in order to produce cleaner and more uniform films. Conventional wisdom in the industry is that macro-particles in general are deleterious to the quality of deposited films.

In contrast, an increased amount of macro particles has been found to result in an effective way to control the anti-bacterial activity of silver oxide films. For a quick release of silver into the surrounding tissue, a thick, fairly macro-particle free coating of pure AgO can be applied. For a more tuned release, a time-release scheme is used.

When depositing a coating on a substrate using cathodic arc, the relative amount of macro-particles ejected from the target can be controlled. Macro-particles are molten blobs of metal that are ejected from the target without being fully vaporized. These blobs are dense and comprised of pure target material. The surfaces of these blobs usually are charged, while the bulk of the material is neutral.

When the macro particles pass through the plasma, the outside surface is oxidized, forming an "coated candy" like structure with a coating of AgO on the outside of the particle and pure silver on the inside. This acts like a time-release capsule.

Time-release effects occur due to the inherent instability of the outer "shell" of AgO and a more stable inner "shell" of pure silver. The silver oxide outer coating releases its anti-microbial activity relatively quickly, killing any bacteria in the surrounding area. During the release process, the inner pure silver is oxidized and slowly released to maintain anti-microbial activity over time. The time period is determined by the size of the macro-particle. Thus, specific coatings of specific sizes of macro-particles can be designed to maintain anti-microbial activity for a selected time period. Typical size ranges for macro-particles are 10 nm to 10 microns, depending on the length of time desired to maintain activity.

Elution is an important factor in anti-microbial activity; however the amount of silver eluted is related to the anti-microbial activity of a Ag/AgO coated device. The elution rate must occur at a certain level in order to be effective against infection and biofilm formation. The minimum rate is approximately 0.005 mg Ag per square inch (0.0048 mg/sq inch). The anti-microbial activity of a silver oxide coating prepared by the method disclosed herein will elute at this rate for at least 60 days. Silver/silver oxide coatings prepared by other methods do not elute at a constant rate for longer than a 7 day period.

Another important feature of the present invention is the ability to imbed a silver oxide coating into the surface of the device, thus obtaining superior adhesion compared to coatings deposited by other deposition methods. The imbedding process can be controlled by using the arc control method at a specific distance from the target, so that coatings embedded up to 100 nm and more for plastics and up to 10 nm and more for metals and ceramics can be obtained.

A suitable device for carrying out the ionic plasma deposition process is illustrated in FIG. 1. As shown in FIG. 1, a cathode 1 of the target material is disposed within a vacuum chamber 4. The cathode 1 is ionized by generating an arc at the cathode from a power supplied by a power source 5 to the cathode. The plasma constituents are selected, controlled or directed toward the substrate by a controlling mechanism 3 that moves the substrate 2 toward or away from the target 1.

Figure 2:
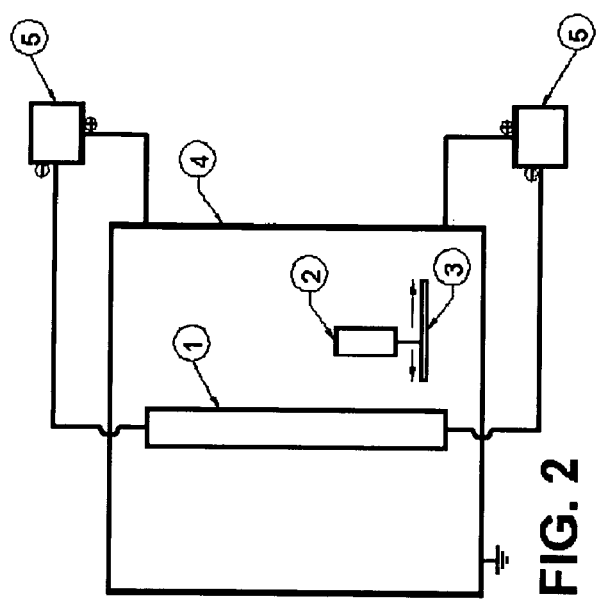
FIG. 2 is another embodiment of the IPD apparatus. 1. Target material, 2. Substrate being coated, 3. Mechanism that has the ability to move the substrate closer or further away from the target, 4. Vacuum chamber, 5. Power supply for the target, and 6. Arc control that determines the speed of the arc.

Additional control of the power supply 6 as shown in FIG. 2 can also be used to provide further control of the plasma constituents by controlling arc speed.

In the case where the desired anti-microbial metal is silver, for example, a silver cathode is placed in the vacuum chamber of the ionic plasma deposition device, along with a selected substrate. The silver used as the cathode is preferably medical grade (i.e. 99.99% pure) silver to avoid any potentially toxic materials, although silver metal of lower purity can also be used.

The vacuum chamber is pumped to a suitable working pressure typically in the range of 0.1 mT to 30 mT; however, the ability of the IPD process to produce effective anti-microbial surfaces having sustained release rates is not dependent on any specific working pressure within the typical range of 0.1 mT to 30 mT. Similarly, the ionic plasma deposition process is not dependent upon operating temperature. Typical operating temperatures are in the range of 25 to 75° C. and any temperature within this range is suitable for producing anti-microbial surfaces.

The substrate can be rotated, such as on turntables, or rolled past the deposition area in any orientation relative to the trajectory of the incoming deposition material. Power is supplied to the cathode to generate an electric arc at the cathode. This power can range from a few amps of current to several hundred amps, at a voltage appropriate for the source material. Voltage is typically in the range of 12 volts to 60 volts, and is appropriately scaled to the size of the source material, which can be a few inches to several feet in length. The electric arc ionizes the silver metal cathode into a plasma of silver ions, neutrally charged particles and electrons. Oxygen is introduced into the plasma at a typical rate of 10 to 1000 sccm and combines with the silver ions to form silver oxide particles. The silver oxide particles can have a particle size ranging from less than 1 nanometer to about 50 microns, depending upon the desired ion release rate and ultimate use of the substrate.

It is also possible to control the metal ion release rate of the anti-microbial surfaces in order to obtain an effective release rate over a sustained period of time. Such controlled metal release is obtained by depositing a combination of oxides of various structures, including monovalent, divalent and multivalent oxides, onto the substrate. Combinations of oxides exhibit different ion release rates which contribute to the control of ion concentrations and the sustained release of the metal ions for enhanced anti-microbial activity. Multivalent oxides can also be created on neutral metal particles as they are oxidized in the plasma. This further enhances the sustained release of the deposited materials by creating combinations of oxides of various sizes and valence states. The benefit of such combinations is an increase in ion release over a longer period of time. The silver oxide particles are then deposited onto the substrate surface in the form of a dispersion of silver oxide particles.

The effectiveness of the anti-microbial surface in delivering an anti-microbial response is also dependent upon the processing time for forming the anti-microbial surface. Longer processing times from 5 seconds to multiple minutes result in anti-microbial surfaces having different anti-microbial responses.

Controlled metal release is also obtained by depositing a combination of different metal oxides onto the substrate. These combinations include silver and titanium, silver and gold, silver and copper, silver copper and gold. Other materials can be combined as co-deposited metals, alloys or as alternating layers in various combinations. Control and flexibility of the plasma environment allows a much larger range of combinations and, accordingly, a wide range of customized coatings.

The invention is further illustrated by the following non-limiting examples.

EXAMPLES

Materials and Methods

Sample Elution Testing—Elution testing was performed to determine the silver elution profile of coated Polypropylene samples. Silver elution testing provides a quantitative method for determining the amount of silver released from the test article over a specified period of time. The testing was conducted according to the current FDA Good Laboratory Practice, GLP, Standards, 21 CFR, Part 58. Each test article was extracted in USP 0.9% NaCl for injection at a temperature of 37°±1° C. for silver elution analysis by Inductively Coupled Plasma (ICP) Spectroscopy. Each sample is separately placed in 10 mL of USP 0.9% NaCl for a specified period of time. The time periods used during this study were 15 min., 30 min., 1 hr, 2 hr, 4 hr, 8 hr, 24 hr, days 2-7, day 10, day 15, day 20, day 25, and day 30. At each time point, the fluid surrounding the sample was decanted into a clean glass container and fresh NaCl was added to the sample container. The decanted liquid was brought to a total volume of 50 mL with deionized water, then acid digested and examined by ICP for silver content.

Sample Zone of Inhibition (ZOI) Testing—ZOI testing is an easy, 24 hour test anti-microbial activity. The test is not quantitative, and only provides enough information to indicate if a serial dilution test is warranted. This test provides no information regarding tissue re-growth or necrosis.

Sample Serial Dilution Testing—Serial dilution testing provides an accurate measure of the amount of bacteria per given volume. When compared to a control sample, it can provide a quantitative measure of anti-microbial coating activity.

A standard bacterial solution is prepared from a 0.5 McFarland standard (SOURCE?). The standard is calibrated to read between 0.08 and 0.1 OD at 625 nm, which gives a standardized bacterial count of $1.5 \times 10^8$ cfu/mL.

While the following embodiments of the present invention have been described in detail, it is apparent that modifications and adaptations of those embodiments will occur to those of skill in the art. It is to be understood that such modifications are within the scope of the invention.

Example 1

Silver Coated Catheter (Published Method)

A solver-coated catheter was prepared using the same procedure described in Example 6 of U.S. Pat. No. 5,454,886. Silver metal was deposited on 2.5 cm sections of a latex Foley catheter using magnetron sputtering. Operating conditions were performed as closely as possible based on the published example; i.e., the deposition rate was 200 A° per minute; the argon working gas pressure was 30 m Torr; and the ratio of temperature of substrate to melting point of the coating metal silver, T/Tm was 0.30. In this example the angles of incidence were variable since the substrate was round and rough; that is, the angles of incidence varied around the circumference and, on a finer scale, across the sides and tops of the numerous surface features. The anti-microbial effect on *S. aureus* was tested by a zone of inhibition, (Table 1).

TABLE 1

|  | Reported Results 5,454,886 patent | Experimental Results |
|---|---|---|
| Zone of inhibition | 0.5 mm | |
| T/Tm | 0.38 | |
| Zone of inhibition | 16 mm | <1 mm |
| T/Tm | 0.30 | 0.30 |

Under the same T/Tm conditions, previously published, and repeating the same conditions as set forth in Example 6 of the U.S. Pat. No. 5,454,889, the observed zone of inhibition (ZOI) around the tubing was significantly less than the reported ZOI. The ZOI test was performed using *S. aureus* as reported in example 1 of the '5,454,886 patent.

Example 2

DC Magnetron Sputtered Antimicrobial Coating (Published Method)

The procedure of Example 7 in the U.S. Pat. No. 5,454,886 was followed. A Teflon coated latex Foley catheter was coated by DC magnetron sputtering 99.99% pure silver on the surface using the conditions used were: 0.5 kW power, 40 mTorr Ag/O$_2$, 20 degrees C. initial substrate temperature, a cathode/anode distance of 100 mm, and a final film thickness of 300 nm. The working gases used were commercial Ag and 99/1 wt % Ag/O$_2$.

The anti-microbial effect of the coating was tested by a zone of inhibition test. Mueller Hinton agar was dispensed into Petri dishes. The agar plates were allowed to surface dry prior to being inoculated with a lawn of *Staphylococcus aureus* ATCC#25923. The inoculant was prepared from Bactrol Discs (Difco, M.) which were reconstituted per the manufacturer's directions. Immediately after inoculation, the coated materials to be tested were placed on the surface of the agar. The dishes were incubated for 24 hr. at 37° C. After the incubation period, the ZOI was measured and a corrected zone of inhibition was calculated as follows: corrected zone of inhibition=zone of inhibition-diameter of the test material in contact with the agar. The published results showed no zone of inhibition for the uncoated samples. A corrected zone of inhibition of 11 mm was reported for catheters sputtered in the 99/1 wt % Ag/O$_2$ using a working gas pressure of 40 mTorr.

The experiment was repeated under the published conditions listed in Table 2. A small ZOI of less than one mm was observed.

TABLE 2

Conditions of DC Magnetron Sputtering Used for Anti-Microbial Coatings

| Samples Sputtered in Commercial Argon | | Samples Sputtered in 99/1 wt % Ar/O$_2$ | |
|---|---|---|---|
| Power | 0.1 kW | Power | 0.5 kW |
| Argon Pressure: | 5 m Torr | Ag/O$_2$ Pressure: | 40 m Torr |
| Initial Substrate Temperature: | 20° C. | Initial Substrate Temperature: | 20° C. |
| Cathode/Anode Distance: | 40 mm | Cathode/Anode Distance: | 100 mm |
| Film Thickness: | 2500 Å | Film Thickness: | 3000 Å |
| ZOI (reported) | 0 | | 11 mm |
| Experimental (repeat under published conditions above) Results | | | |
| ZOI | 0 | | <1 mm |

In repeating the above published conditions, the experimental results showed a small ZOI of less then one mm.

Example 3

Composite Silver Anti-Microbial Films (Published Method)

This example demonstrates a state of the art procedure for preparing a composite anti-microbial coating formed by reactive sputtering as found in Example 1 of the U.S. Pat. No. 5,454,886. Table 3 lists the published sputtering conditions and the conditions used for the comparison study compared with Experimental results obtained by following the steps in the published procedure.

TABLE 3

| Sputtering Conditions | | |
|---|---|---|
| | Published | Experimental |
| Target | 99.99% Ag | 99.99% |
| Working gas | 80/20% Ar/O2 | 80/20% ArO2 |
| Working gas P | 2.5-50 mTorr | 40 mTorr |
| Power | 0.1-2.5 kW | 0.5 kW |
| Substrate T | −5 to 20° C. | 20° C. |
| Anode/Cathode Distance | 40 to 100 mm | 100 mm |
| Base P | $<4 \times 10^{-4}$ Torr | |
| ZOI | 6-12 mm | 0 to 2 mm |

Example 4

In Vitro Testing of Silver Oxide Coated Catheters

This example demonstrates the effectiveness of the antimicrobial coating over a range of gram positive and gram negative organisms. The organisms tested for general zone of inhibition were: Gram positive bacteria *E. faecalis*, *S. aureus* MR, and *S. epidermis*. Gram negative bacteria were *E. coli*, *K. pneumoniae*, and *P. aerugosia*.

The method used to test for a ZOI was plate-to-plate transfer maximum for 4 days. Each of the above listed bacteria was plated out on tryptic soy agar. The pre-made plate was inoculated with the bacterium, divided into three equal sections, and a one inch long Foley catheter sample coated with 200 nm of silver oxide was placed in the center of each part after inoculation. The samples were placed in an incubator at 37° C. and the ZOI was measured at 24, 48, 72 and 96 hours.

Total ZOI is defined as the ZOI minus the width of the sample. For this experiment, measurements were made of the total ZOI and divided in half. If there was no measurable ZOI and no biofilm, and organism did not grow over or attach to the sample, the measurement was noted as 0.0 mm. When a biofilm was observed, it was recorded as −11.0 mm. Plate to plate transfer was repeated until a biofilm was noted or a measurement of 0.0 mm was recorded for 2 transfers. Each organism had three plates and each plate had three data points for the side-by-side sample and control catheter. Measurements were taken daily. The three measurements per plate were averaged to get a daily plate ZOI. This was done to compensate for swipes being too heavy or light in concentration. All measurements taken were recorded in mm. A measurement of 0.0 indicated that the organism grew to the silver sample but did not adhere or create a biofilm on the silver sample catheter. All control samples had biofilms from Day 1 without exceptions. Results are shown in Table 4.

TABLE 4

| | Day 1 | | | | | | | | |
|---|---|---|---|---|---|---|---|---|---|
| | Plate 1 Zone Width (mm) | Plate 1 ZOI | Control Plate 1 | Plate 2 Zone Width (mm) | Plate 2 ZOI | Control Plate 2 | Plate 3 Zone Width (mm) | Plate 3 ZOI | Control Plate 3 |
| *E. faecalis* (+) | | | | | | | | | |
| Day 1 | 2.0 | 1.0 | 0.0 | 3.0 | 1.5 | 0.0 | 1.0 | 0.5 | 0.0 |
| | 3.0 | 1.5 | 0.0 | 4.0 | 2.0 | 0.0 | 4.0 | 2.0 | 0.0 |
| | 3.0 | 1.5 | 0.0 | 3.0 | 1.5 | 0.0 | 3.0 | 1.5 | 0.0 |
| Day 2 | 0.0 | 0.0 | 0.0 | 0.0 | 0.0 | 0.0 | 0.0 | 0.0 | 0.0 |
| | 0.0 | 0.0 | 0.0 | 0.0 | 0.0 | 0.0 | 0.0 | 0.0 | 0.0 |
| | 0.0 | 0.0 | 0.0 | 0.0 | 0.0 | 0.0 | 0.0 | 0.0 | 0.0 |
| Day 3 | 0.0 | 0.0 | 0.0 | 0.0 | 0.0 | 0.0 | 2.0 | 1.0 | 0.0 |
| | 0.0 | 0.0 | 0.0 | 0.0 | 0.0 | 0.0 | 3.0 | 1.5 | 0.0 |
| | 0.0 | 0.0 | 0.0 | 0.0 | 0.0 | 0.0 | 4.0 | 2.0 | 0.0 |
| *S. epidermis* (+) | | | | | | | | | |
| Day 1 | 3.0 | 1.5 | 0.0 | 9.0 | 4.5 | 0.0 | 2.0 | 1.0 | 0.0 |
| | 3.0 | 1.5 | 0.0 | 12.0 | 6.0 | 0.0 | 9.0 | 4.5 | 0.0 |
| | 8.0 | 4.0 | 0.0 | 10.0 | 5.0 | 0.0 | 8.0 | 4.0 | 0.0 |
| Day 2 | 1.0 | 0.5 | 0.0 | 0.0 | 0.0 | 0.0 | 2.0 | 1.0 | 0.0 |
| | 0.0 | 0.0 | 0.0 | 1.0 | 0.5 | 0.0 | 4.0 | 2.0 | 0.0 |
| | 2.0 | 1.0 | 0.0 | 0.0 | 0.0 | 0.0 | 2.0 | 1.0 | 0.0 |
| Day 3 | 3.0 | 1.5 | 0.0 | 6.0 | 3.0 | 0.0 | 5.0 | 2.5 | 0.0 |
| | 0.0 | 0.0 | 0.0 | 4.0 | 2.0 | 0.0 | 6.0 | 3.0 | 0.0 |
| | 2.0 | 1.0 | 0.0 | 3.0 | 1.5 | 0.0 | 6.0 | 3.0 | 0.0 |
| Day 4 | 1.0 | 0.5 | 0.0 | 2.0 | 1.0 | 0.0 | 0.0 | 0.0 | 0.0 |
| | 4.0 | 2.0 | 0.0 | 2.0 | 1.0 | 0.0 | 2.0 | 1.0 | 0.0 |
| | 2.0 | 1.0 | 0.0 | 2.0 | 1.0 | 0.0 | 2.0 | 1.0 | 0.0 |

TABLE 4-continued

| | Plate 1 Zone Width (mm) | Plate 1 ZOI | Control Plate 1 | Plate 2 Zone Width (mm) | Plate 2 ZOI | Control Plate 2 | Plate 3 Zone Width (mm) | Plate 3 ZOI | Control Plate 3 |
|---|---|---|---|---|---|---|---|---|---|
| *E. Coli* (−) | | | | | | | | | |
| Day 1 | 2.0 | 1.0 | 0.0 | 5.0 | 2.5 | 0.0 | 0.0 | 0.0 | 0.0 |
| | 7.0 | 3.5 | 0.0 | 2.0 | 1.0 | 0.0 | 0.0 | 0.0 | 0.0 |
| | 1.0 | 0.5 | 0.0 | 10.0 | 5.0 | 0.0 | 6.0 | 3.0 | 0.0 |
| Day 2 | 0.0 | 0.0 | 0.0 | 4.0 | 2.0 | 0.0 | 0.0 | 0.0 | 0.0 |
| | 4.0 | 2.0 | 0.0 | 5.0 | 2.5 | 0.0 | 0.0 | 0.0 | 0.0 |
| | 2.0 | 1.0 | 0.0 | 2.0 | 1.0 | 0.0 | 0.0 | 0.0 | 0.0 |
| Day 3 | 2.0 | 1.0 | 0.0 | 4.0 | 2.0 | 0.0 | 0.0 | 0.0 | 0.0 |
| | 1.0 | 0.5 | 0.0 | 4.0 | 2.0 | 0.0 | 0.0 | 0.0 | 0.0 |
| | 1.0 | 0.5 | 0.0 | 3.0 | 1.5 | 0.0 | 0.0 | 0.0 | 0.0 |
| Day 4 | 0.0 | 0.0 | 0.0 | 0.0 | 0.0 | 0.0 | 0.0 | 0.0 | 0.0 |
| | 0.0 | 0.0 | 0.0 | 2.0 | 1.0 | 0.0 | 0.0 | 0.0 | 0.0 |
| | 0.0 | 0.0 | 0.0 | 2.0 | 1.0 | 0.0 | 0.0 | 0.0 | 0.0 |
| *K. pneumoniae* (−) | | | | | | | | | |
| Day 1 | 1.0 | 0.5 | 0.0 | 1.0 | 0.5 | 0.0 | 1.0 | 0.5 | 0.0 |
| | 3.0 | 1.5 | 0.0 | 4.0 | 2.0 | 0.0 | 4.0 | 2.0 | 0.0 |
| | 2.0 | 1.0 | 0.0 | 1.0 | 0.5 | 0.0 | 2.0 | 1.0 | 0.0 |
| Day 2 | 0.0 | 0.0 | 0.0 | 0.0 | 0.0 | 0.0 | 0.0 | 0.0 | 0.0 |
| | 1.0 | 0.5 | 0.0 | 4.0 | 2.0 | 0.0 | 3.0 | 1.5 | 0.0 |
| | 0.0 | 0.0 | 0.0 | 0.0 | 0.0 | 0.0 | 0.0 | 0.0 | 0.0 |
| Day 3 | 0.0 | 0.0 | 0.0 | 0.0 | 0.0 | 0.0 | 2.0 | 1.0 | 0.0 |
| | 0.0 | 0.0 | 0.0 | 0.0 | 0.0 | 0.0 | 3.0 | 1.5 | 0.0 |
| | 0.0 | 0.0 | 0.0 | 0.0 | 0.0 | 0.0 | 4.0 | 2.0 | 0.0 |
| *P. aerugosia* (−) | | | | | | | | | |
| Day 1 | 1.0 | 0.5 | 0.0 | 6.0 | 3.0 | 0.0 | 2.0 | 1.0 | 0.0 |
| | 2.0 | 1.0 | 0.0 | 7.0 | 3.5 | 0.0 | 4.0 | 2.0 | 0.0 |
| | 1.0 | 0.5 | 0.0 | 5.0 | 2.5 | 0.0 | 2.0 | 1.0 | 0.0 |
| Day 2 | 0.0 | 0.0 | 0.0 | 4.0 | 2.0 | 0.0 | 1.0 | 0.5 | 0.0 |
| | 1.0 | 0.5 | 0.0 | 5.0 | 2.5 | 0.0 | 0.0 | 0.0 | 0.0 |
| | 1.0 | 0.5 | 0.0 | 4.0 | 2.0 | 0.0 | 1.0 | 0.5 | 0.0 |
| Day 3 | 0.0 | 0.0 | 0.0 | 3.0 | 1.5 | 0.0 | 2.0 | 1.0 | 0.0 |
| | 0.0 | 0.0 | 0.0 | 3.0 | 1.5 | 0.0 | 3.0 | 1.5 | 0.0 |
| | 0.0 | 0.0 | 0.0 | 3.0 | 1.5 | 0.0 | 4.0 | 2.0 | 0.0 |
| *S. aureus* MR (+) | | | | | | | | | |
| Day 1 | 2.0 | 1.0 | 0.0 | 5.0 | 2.5 | 0.0 | 1.0 | 0.5 | 0.0 |
| | 3.0 | 1.5 | 0.0 | 2.0 | 1.0 | 0.0 | 2.0 | 1.0 | 0.0 |
| | 2.0 | 1.0 | 0.0 | 10.0 | 5.0 | 0.0 | 0.0 | 0.0 | 0.0 |
| Day 2 | 3.0 | 1.5 | 0.0 | 4.0 | 2.0 | 0.0 | 0.0 | 0.0 | 0.0 |
| | 2.0 | 1.0 | 0.0 | 5.0 | 2.5 | 0.0 | 0.0 | 0.0 | 0.0 |
| | 5.0 | 2.5 | 0.0 | 2.0 | 1.0 | 0.0 | 0.0 | 0.0 | 0.0 |
| Day 3 | 0.0 | 0.0 | 0.0 | 4.0 | 2.0 | 0.0 | 3.0 | 1.5 | 0.0 |
| | 0.0 | 0.0 | 0.0 | 4.0 | 2.0 | 0.0 | 4.0 | 2.0 | 0.0 |
| | 0.0 | 0.0 | 0.0 | 3.0 | 1.5 | 0.0 | 3.0 | 1.5 | 0.0 |
| Day 4 | 0.0 | 0.0 | 0.0 | 0.0 | 0.0 | 0.0 | 2.0 | 1.0 | 0.0 |
| | 0.0 | 0.0 | 0.0 | 2.0 | 1.0 | 0.0 | 3.0 | 1.5 | 0.0 |
| | 0.0 | 0.0 | 0.0 | 2.0 | 1.0 | 0.0 | 3.0 | 1.5 | 0.0 |

Example 5

In Vivo Testing of a Silver Oxide Coated Catheter

This example demonstrates in vivo testing of two identical pieces of catheter material with a 200 nm silver oxide coating in a rabbit. The test devices were ETO-sterilized. For each of the two catheter pieces, four segments of the antimicrobial portion of the catheter (approximately 4 inches in length) were prepared. The test devices were used as provided and maintained at room temperature.

A total of eight catheter segments (four segments of each catheter material) were implanted into a female New Zealand White rabbit. Prior to implantation on Day 1, the animal was weighed and anesthetized with an intravenous injection of a ketamine/xylazine cocktail (87 mg/mL ketamine, 13 mg/mL xylazine) at 0.1 mL/kg. The animal was 23-25 weeks old and weighed 2.63 kg on Day 1.

One week following catheter implantation, a challenge organism (*S. aureus* or *E. coli*) was placed on the skin around each catheter entry site (two segments of each catheter material challenged with *S. aureus* and the remaining two segments of each catheter material challenged with *E. coli*). The animal was sacrified 48 hours following bacterial challenge.

The treatment parameters are described below in Table 5. The bacterial challenge took place on Day 8, in accordance with the the protocol used

TABLE 5

| Group | No. | Implantation (8 implant sites) | Route | Implant Site | Bacterial Challenge | Necropsy (Day) |
|---|---|---|---|---|---|---|
| A | 1 | 1 catheter segment/site | Percutaneous | Perispinal | Day 8 | Day 10 |

The paravertebral area was clipped with electric clippers and prepared with povidone iodine and 70% alcohol. The animal had eight implantation sites along the back. Each site was 2.5-5.0 cm from the midline and sites were approximately 2.5 cm apart. Implant sites were identified by permanent marker.

At each implant site, the skin was punctured into the muscle with a 16-gauge needle. The catheter segment was fed down the ID of the needle into the muscle and the needle removed, leaving half of the catheter segment implanted through the skin into the muscle. One section of catheter material was implanted at each site. The rabbit was implanted with four segments of each of the two identical pieces, for a total of eight catheter segment was covered with a sterile dressing. Locations the animal's back are identified in Table 6.

TABLE 6

| Site No. | Side | Region | Implanted Material |
|---|---|---|---|
| 1 | Left | Cranial | 3659-16 |
| 2 | Left | Cranial - Middle | 3659-16 |
| 3 | Left | Caudal - Middle | 3659-17 |
| 4 | Left | Caudal | 3659-17 |
| 5 | Right | Cranial | 3659-16 |
| 6 | Right | Cranial - Middle | 3659-16 |
| 7 | Right | Caudal - Middle | 3659-17 |
| 8 | Right | Caudal | 3659-17 |

On Day 8, the sterile dressing was removed from each exposed catheter segment. The skin around each catheter entry site received a surface instillation of a 1 mL suspension containing $2.2 \times 10^5$ CFU/mL of S. aureus or $5.10 \times 10^2$ CFU/mL of E. coli. One segment of each catheter material was challenged with S. aureus and one segment of each catheter material was challenged with E. coli. Following inoculation, the catheter segments were re-covered with a sterile dressing. The inoculating organism used at each site is listed in Table 7.

TABLE 7

| Site No. | Side | Region | Implanted Material | Inoculating Organism | Comments |
|---|---|---|---|---|---|
| 1 | Left | Cranial | 3659-16 | S. aureus | Administered 1 mL bacteria suspension topically |
| 2 | Left | Cranial - Middle | 3659-16 | N/A[1] | N/A |
| 3 | Left | Caudal - Middle | 3659-17 | N/A[1] | N/A |
| 4 | Left | Caudal | 3659-17 | N/A[1] | N/A |
| 5 | Right | Cranial | 3659-16 | N/A[1] | N/A |
| 6 | Right | Cranial - Middle | 3659-16 | E. coli | Administered 1 mL bacteria suspension topically |
| 7 | Right | Caudal - Middle | 3659-17 | E. coli | Administered 1 mL bacteria suspension topically |
| 8 | Right | Caudal | 3659-17 | S. aureus | Administered 1 mL bacteria suspension topically |

N/A = Not applicable

On Day 10, the animal was euthanized with an intravenous injection of a commercial euthanasia solution according to Brain Chemistry Optimization Program protocol 01-11-21-22-02-026. The entire implant was collected aseptically and submitted for quantitative bacterial determination. A superficial swab of the tract area of muscle and skin was taken. Swabs were not collected in this study because several catheters had backed out and the implant tract was not visible. A portion of the muscle around the implant tract was placed in 10% neutral buffered formalin and submitted to Colorado Histo-Prep (Fort Collins, Colo.) for evaluation by a board-certified veterinary pathologist. For four of the eight implant sites (Site Nos. 1, 6, 7, and 8), the internal and external portions of the implant were collected separately into Tryptic Soy Broth. These were the sites that still had a portion of the catheter exiting the skin.

Clinical observations showed the rabbit remained health and showed no signs of infection, as seen in Table 8.

TABLE 8

Clinical observations of rabbit health

| Group | Animal No. | Day | Clinical Observations | | |
|---|---|---|---|---|---|
| | | | General | Stool | Appetite |
| A | I7 | 2-3 | G0 | S0 | A0 |
| | | 4-5 | G0 | S1 | A0 |
| | | 6-8 | G0 | S0 | A0 |
| | | 9-10 | G0 | S1 | A0 |

Key:
G0 = Appeared normal; bright, alert, and responsive
S0 = Stool normal
S1 = Stool soft
A0 = Normal amount of food consumed For each test material, one implant site was inoculated with S. aureus and one implant site was inoculated with E. coli (Site Nos. 1, 6, 7, and 8). For the inoculated sites, two implant locations, identified as internal and external, were evaluated for microbial growth and identification. The catheter sections above the skin were identified as the external implant sites and the catheter sections below the skin were identified as the internal implant sites.

For the remaining four implant sites (Site Nos. 2-5), no inoculation was performed, as there was no visible implant external to the skin on the day of inoculation (Day 8). For these sites, subcutaneous portions of the catheter were evaluated for microbial growth and identification.

For the site implanted with the 3659-16 catheter material and challenged with S. aureus (Site No. 1), positive growth of the challenge organism was identified at both the internal and external implant sites. For the site implanted with the 3659-16 catheter material and challenged with E. coli (Site No. 6), bacterial growth identified as Staphylococcus hominis was present at the internal implant site; this growth was due to environmental contamination. At this site, no growth of the challenge organism (E. coli) was identified at the internal or external implant site.

For the site implanted with the 3659-17 catheter material and challenged with S. aureus (Site No. 8), positive growth of the challenge organism was identified at the external implant site only. For the site implanted with the 3659-17 catheter material and challenged with E. coli (Site No. 7), no growth was present at the internal or external implant site.

For the remaining four implant sites, which were not inoculated (Site Nos. 2-5), no bacterial growth was present. See Table 9.

TABLE 9

Microbiological Growth Results From Implant sites

| Group | Animal No. | Implant Site | Implanted Material | Challenge Organism | Culture results | Bacterial ID |
|---|---|---|---|---|---|---|
| A | I7 | 1 - Internal | 3659-16 | S. aureus | Positive Growth | S. aureus |
| | | 1 - External | 3659-16 | S. aureus | Positive Growth | S. aureus |
| | | 2 | 3659-16 | No bacteria applied | No Growth | N/A |
| | | 3 | 3659-17 | No bacteria applied | No Growth | N/A |
| | | 4 | 3659-17 | No bacteria applied | No Growth | N/A |
| | | 5 | 3659-16 | No bacteria applied | No Growth | N/A |
| | | 6 - Internal | 3659-16 | E. coli | Positive Growth | S. hominis |
| | | 6 - External | 3659-16 | E. coli | No Growth | N/A |
| | | 7 - Internal | 3659-17 | E. coli | No Growth | N/A |
| | | 7 - External | 3659-17 | E. coli | No Growth | N/A |
| | | 8 - Internal | 3659-17 | S. aureus | No Growth | N/A |
| | | 8 - External | 3659-17 | S. aureus | Positive Growth | S. aureus |

N/A = Not applicable

There was no grossly visible evidence of tissue reaction or infection at any of the implant sites. For all implant sites, there was black to gray discoloration of the subcutaneous fascia and muscle at location of the implant. Results are summarized in Table 10.

TABLE 10

Necropsy observations

| Group | Animal No. | Implant Site No. | Implanted Material | Location Condition | General Observations[2] |
|---|---|---|---|---|---|
| A | I7 | 1 | 3659-16 | Catheter pulled out of muscle | No grossly visible evidence of tissue reaction or infection |
| | | 2 | 3659-16 | Portion of catheter in muscle, Did back out half way | No grossly visible evidence of tissue reaction or infection |
| | | 3 | 3659-17 | Portion of catheter in muscle | No grossly visible evidence of tissue reaction or infection |
| | | 4 | 3659-17 | Portion of catheter still in muscle | No grossly visible evidence of tissue reaction or infection |
| | | 5 | 3659-16 | Portion of catheter still in muscle | No grossly visible evidence of tissue reaction or infection |
| | | 6 | 3659-16 | Catheter pulled out of muscle | No grossly evisible vidence of tissue reaction or infection |
| | | 7 | 3659-17 | Catheter pulled out of muscle | No grossly visible evidence of tissue reaction or infection |
| | | 8 | 3659-17 | Catheter pulled out of muscle | No grossly visible evidence of tissue reaction or infection |

The results showed that the silver/silver oxide impregnated antimicrobial catheters prevented the formation of bacteria, bacterial colonies, and biofilms. The antimicrobial results were consistent across all implant sites, and the antimicrobial coating remained effective even following a microbial challenge at Day 8 with E. coli or S. aureus. There was no necrosis observed. The lesions were consistent with a foreign body reaction in the muscle, with a more acute inflammatory reaction in the subcutaneous tissue.

Example 6

Elution of Silver Oxide Coating

A total of twenty test samples, one $cm^2$ polypropylene coated with the typical silver oxide coating were evaluated. Two samples were taken from a total of ten different samples for both the test groups. The testing was performed in duplicate using inductively coupled plasma analysis to determine the amount of silver present at each time point. The values were then averaged for a total of ten reported values for each test group. The elution values are given as mg/sample, which in this case is mg/square inch.

The samples all exhibited a consistent behavior over the first 24 hours in the NaCl solution. There was a slight peak around the four hour time point, before the values leveled off around the 24 hour time point.

All of the samples were very consistent in their behavior. The values were fairly stable from day 1 through day 5; the values then peaked around the 6 day time point and then leveled off from day 7 through day 30.

The average elution for the coated Polypropylene samples over all time points is approximately 0.005 mg per square inch (0.0048 mg/sq inch). The samples show a fairly consistent silver elution over the entire length the study with slight peaks noted at the 4 hour time point and after 6 days in saline solution. Using the elution values and an approximate total silver value of 1.05 mg per sq inch (obtained from outside testing) for the Polypropylene.

Example 7

In Vivo Healing Test of ePTFE Coated Substrate

This example demonstrates through in vivo testing the ability of the 200 nm silver oxide coating to not cause necrosis. 1 cm² ePTFE samples were coated with the standard 200 nm silver oxide coating and implanted in a rabbit subcutaneously as outlined in example 6 above. The substrates were explanted at 9 and 22 days to study the healing of the tissue surrounding the implanted silver oxide coated part. The results are outlined in Table 11.

TABLE 11

Histology report on 200 nm silver oxide coating

| Treatment Group | Implant Duration, Days | ePTFE//visceral surface | ePTFE//meshwork surface | Silver particles/particulate observations |
|---|---|---|---|---|
| Control uncoated mesh | 9 | One to several mps layers; 10 + layers sscs with ncf | MF: surrounded by mps w occ gcs w ncf Mesh: filled w mps w ncf; occ pmns & baso | None |
| | 22 | Modestly thin fibrotic response comprised of fibroblasts (spindle-shaped cells) within a collagen matrix. Macrophages & occ giant cells at interface. | Fibrotic response at ePTFE surface continuous with response within meshwork and surrounding monofilament elements. | None |
| Silver oxide coated mesh Sample 1 200 nm | 9 | One to several layers of large mps. Fibrotic overlay suggest loss of nuclei. Nucleoysis. Prominent gcs | MF: Dec nos of mps Mesh: Sparsely cellular fibrin network. Tissue debris. Focal areas of necrotic debris | Prominent gcs with parts Occ larger silver particles Continuous lamina of mps w parts - vis surface. |
| | 22 | Typicla fibrotic response' noted. Black ppt (matched to refractile debris) noted within macropnhoges with response. Ref. debris wi mps & gcs at interface. | Fibrotic response at TFE surface. Abundant baso/mast cells within response. Occ black ppt (ref debris) noted. Ref. debris wi mps & gcs at interface, | Black ppt matched to refreactile debris noted with mps & gcs both within fibrotic response and at TFE interface |
| Silver oxide coated mesh Sample 2 200 nm | 9 | One to several layers of mps Modest ncf | MF: surrounded by mps w occ gcs//slightly reduced Mesh: Modest ncf w mps; prominent vascular response | Freq Ag particulates wi mps. Mostly intracellular Fibrotic lamina (vis surface) - parts wi mps |
| | 22 | Typical fibrotic response' noted. Scattered mps w black ppt (refractile) debris & lamina pattern w mps containing black ppt. TFE surface lined by mps wo debris | Fibrotic response at TFE surface. Occ scattered mps w black ppt | Scattered ppt wi mps wi meshwork response and visceral response. |

Example 8

Cathodic Arc Deposition with Moveable Substrate

This example demonstrates how a moveable substrate affects the macro-particle size, thus controlling the release of the silver oxide.

The substrate, substrate one, was placed in a moveable holder at a distance of 30 inches from the target. The chamber was pumped to a level of 5E-4 Torr. The arc was initiated with a current of 100 amps and 16 volts. Oxygen was introduced into the chamber at a rate of 200 SCCM. The substrate was translated closer to the target at a speed of one inch every 15 seconds. This was continued until the substrate was 8 inches away from the target.

In a complementary experiment, a substrate, substrate two, was placed at a distance of 30 inches from the target with the same current, voltage, total time and rate of oxygen flow. This time, the substrate was left stationary.

Initial ZOI testing showed the same size zone in a 24 hour period. Plate transfer was performed for several bacteria and the results are shown in Table 12. It is seen that the substrate that was moved toward the target during the deposition process showed anti-microbial activity for a longer period of time than did the substrate that was left stationary.

In addition to the ZOI testing, cross sections of the two substrates were examined using SEM analysis. In sample one, the amount and size of macro-particles increased with the thickness of the film; i.e., there were fewer and smaller macro-particles close to the substrate, and the number and size increased as the thickness of the film grew. Conversely, the cross section in sample two was uniform with very few macro-particles.

TABLE 12

| | Day 1 | | | | | |
|---|---|---|---|---|---|---|
| | Substrate 1 | | | Substrate 2 | | |
| | Plate 1 ZOI (mm) | Plate 2 ZOI (mm) | Control Plate | Plate 1 ZOI (mm) | Plate 2 ZOI (mm) | Control Plate |
| *E. faecalis* (+) | | | | | | |
| Day 1 | 4.0 | 4.0 | 0.0 | 3.0 | 3.0 | 0.0 |
| | 4.0 | 4.5 | 0.0 | 4.0 | 2.0 | 0.0 |
| | 3.0 | 4.5 | 0.0 | 3.0 | 2.0 | 0.0 |
| Day 2 | 2.0 | 3.0 | 0.0 | 0.0 | 0.0 | 0.0 |
| | 3.0 | 1.5 | 0.0 | 0.0 | 0.0 | 0.0 |
| | 2.0 | 3.0 | 0.0 | 0.0 | 0.0 | 0.0 |
| Day 3 | 1.0 | 0.5 | 0.0 | 0.0 | 0.0 | 0.0 |
| | 1.0 | 0.5 | 0.0 | 0.0 | 0.0 | 0.0 |
| | 0.5 | 1.0 | 0.0 | 0.0 | 0.0 | 0.0 |
| *S. epidermis* (+) | | | | | | |
| Day 1 | 10.0 | 10.0 | 0.0 | 9.0 | 8.0 | 0.0 |
| | 11.0 | 10.0 | 0.0 | 12.0 | 6.0 | 0.0 |
| | 9.0 | 10.0 | 0.0 | 10.0 | 12.0 | 0.0 |

TABLE 12-continued

| | Day 1 | | | | | |
|---|---|---|---|---|---|---|
| | Substrate 1 | | | Substrate 2 | | |
| | Plate 1 ZOI (mm) | Plate 2 ZOI (mm) | Control Plate | Plate 1 ZOI (mm) | Plate 2 ZOI (mm) | Control Plate |
| Day 2 | 7.0 | 3.5 | 0.0 | 0.0 | 0.5 | 0.0 |
| | 7.0 | 3.5 | 0.0 | 1.0 | 0.0 | 0.0 |
| | 5 | 2.5 | 0.0 | 0.0 | 0.0 | 0.0 |
| Day 3 | 6.0 | 6.0 | 0.0 | 0.0 | 0.5 | 0.0 |
| | 4.5 | 5.0 | 0.0 | 0.0 | 0.0 | 0.0 |
| | 5.0 | 5.0 | 0.0 | 1.0 | 0.0 | 0.0 |
| Day 4 | 1.0 | 2.0 | 0.0 | 0.0 | 0.0 | 0.0 |
| | 4.0 | 2.0 | 0.0 | 0.0 | 0.0 | 0.0 |
| | 2.0 | 1.0 | 0.0 | 0.0 | 0.0 | 0.0 |
| *E. Coli* (−) | | | | | | |
| Day 1 | 5.0 | 6.0 | 0.0 | 5.0 | 6.0 | 0.0 |
| | 7.0 | 6.0 | 0.0 | 8.0 | 4.0 | 0.0 |
| | 1.0 | 5.0 | 0.0 | 10.0 | 9.0 | 0.0 |
| Day 2 | 3.0 | 2.5 | 0.0 | 0.0 | 1.0 | 0.0 |
| | 4.0 | 2.5 | 0.0 | 1.0 | 0.0 | 0.0 |
| | 2.0 | 1.0 | 0.0 | 3.0 | 2.5 | 0.0 |
| Day 3 | 2.0 | 2.0 | 0.0 | 0.0 | 0.0 | 0.0 |
| | 3.0 | 2.5 | 0.0 | 0.0 | 0.0 | 0.0 |
| | 2.0 | 2.0 | 0.0 | 1.0 | 0.5 | 0.0 |
| Day 4 | 1.0 | 0.0 | 0.0 | 0.0 | 0.0 | 0.0 |
| | 1.0 | 0.5 | 0.0 | 0.0 | 0.0 | 0.0 |
| | 0.0 | 1.0 | 0.0 | 0.0 | 0.0 | 0.0 |
| *K. pneumoniae* (−) | | | | | | |
| Day 1 | 3.0 | 4.0 | 0.0 | 2.0 | 2.0 | 0.0 |
| | 3.0 | 2.5 | 0.0 | 4.0 | 3.0 | 0.0 |
| | 2.0 | 3.0 | 0.0 | 2.0 | 3.0 | 0.0 |
| Day 2 | 2.0 | 3.0 | 0.0 | 0.0 | 0.0 | 0.0 |
| | 1.0 | 1.5 | 0.0 | 1.0 | 0.0 | 0.0 |
| | 1.0 | 0.5 | 0.0 | 0.0 | 0.0 | 0.0 |
| Day 3 | 0.0 | 0.0 | 0.0 | 0.0 | 0.0 | 0.0 |
| | 1.0 | 0.5 | 0.0 | 0.0 | 0.0 | 0.0 |
| | 0.0 | 0.0 | 0.0 | 0.0 | 0.0 | 0.0 |
| *P. aerugosia* (−) | | | | | | |
| Day 1 | 10.0 | 12.0 | 0.0 | 6.0 | 6.0 | 0.0 |
| | 12.0 | 12.0 | 0.0 | 7.0 | 6.5 | 0.0 |
| | 10.0 | 10.0 | 0.0 | 5.0 | 6.5 | 0.0 |
| Day 2 | 4.0 | 3.0 | 0.0 | 1.0 | 0.5 | 0.0 |
| | 4.0 | 2.5 | 0.0 | 3.0 | 2.5 | 0.0 |
| | 4.0 | 1.0 | 0.0 | 3.0 | 0.5 | 0.0 |
| Day 3 | 2.0 | 3.0 | 0.0 | 0.0 | 0.0 | 0.0 |
| | 1.5 | 1.0 | 0.0 | 0.0 | 0.0 | 0.0 |
| | 3.0 | 1.5 | 0.0 | 0.0 | 0.0 | 0.0 |
| *S. aureus* MR (+) | | | | | | |
| Day 1 | 12.0 | 14.0 | 0.0 | 6.0 | 7.0 | 0.0 |
| | 13.0 | 12.5 | 0.0 | 4.0 | 7.0 | 0.0 |
| | 12.0 | 10.0 | 0.0 | 12.0 | 10.0 | 0.0 |
| Day 2 | 9.0 | 8.0 | 0.0 | 2.0 | 2.0 | 0.0 |
| | 7.0 | 7.5 | 0.0 | 4.0 | 2.0 | 0.0 |
| | 10.0 | 7.0 | 0.0 | 2.0 | 4.0 | 0.0 |
| Day 3 | 4.0 | 5.0 | 0.0 | 1.0 | 0.0 | 0.0 |
| | 5.0 | 4.5 | 0.0 | 4.0 | 1.0 | 0.0 |
| | 6.0 | 8.0 | 0.0 | 0.0 | 0.0 | 0.0 |
| Day 4 | 1.0 | 2.5 | 0.0 | 0.0 | 0.0 | 0.0 |
| | 2.0 | 3.0 | 0.0 | 0.0 | 0.0 | 0.0 |
| | 1.0 | 0.5 | 0.0 | 0.0 | 0.0 | 0.0 |

Example 9

Arc Control

This example demonstrates how arc control is directly related to the size and frequency of macro-particles produced. In this example, two sample runs were preformed. The first, sample three, had no arc control and the substrate was placed at a distance of 12 inches from the target. The second, sample four, had arc control and the substrate was also placed at a distance of 12 inches from the target. Both samples were placed in the chamber, at separate times for separate runs, and pumped to 5E-4 Torr. The arc was set at 100 Amps for all power supplies to begin with. Each target had two supplies for a starting total of 200 amps. Sample three was run for five minutes with no arc control. Sample four was run with an optimized switching of current at a rate of 300 hertz.

The switching always kept 200 amps on the target, but each power supply was ramped up and down so at any time, the current was not equal on the supplies. This forced the arc to travel a specific distance in a specific time, thereby controlling the macro-particle density and size.

SEM cross sectional analysis was performed on samples three and four. It was observed that, while the films were consistent throughout the entire thickness, sample four had a much larger average of macro-particle size and density then did sample three. The average size of the macro-particles in sample three was approximately one micron with a density of $10^3/cm^2$. The average size of macro-particles in sample four was approximately three microns with a density of $10^4/cm^2$.

Example 10

In Vitro Testing of AgO on Metals

This example demonstrates the effectiveness of the AgO coating on Ti-6-4 and CoCrMo. Samples five and six were cleaned using usual procedures and placed in the vacuum chamber at a distance of 12 inches from the target. The typical silver oxide coating was deposited on the pieces and ZOI testing was done for three days. Sample five was Ti-6-4 and sample six was CoCrMo. Results are summarized in Table 13.

TABLE 13

| | Day 1 | | | | | |
|---|---|---|---|---|---|---|
| | Substrate 5 | | | Substrate 6 | | |
| | Plate 1 ZOI (mm) | Plate 2 ZOI (mm) | Control Plate | Plate 1 ZOI (mm) | Plate 2 ZOI (mm) | Control Plate |
| *S. epidermis* (+) | | | | | | |
| Day 1 | 12.0 | 10.0 | 0.0 | 10.0 | 11.0 | 0.0 |
| | 12.0 | 9.5 | 0.0 | 11.0 | 12.0 | 0.0 |
| | 10.0 | 14.5 | 0.0 | 11.0 | 9.0 | 0.0 |
| Day 2 | 8.0 | 8.5 | 0.0 | 8.0 | 8.0 | 0.0 |
| | 8.0 | 8.5 | 0.0 | 8.0 | 8.5 | 0.0 |
| | 6.0 | 2.5 | 0.0 | 8.0 | 8.0 | 0.0 |
| Day 3 | 5.0 | 6.0 | 0.0 | 5.0 | 4.0 | 0.0 |
| | 4.5 | 3.5 | 0.0 | 6.0 | 7.0 | 0.0 |
| | 4.0 | 3.0 | 0.0 | 6.0 | 4.5 | 0.0 |
| *E. Coli* (−) | | | | | | |
| Day 1 | 5.0 | 2.5 | 0.0 | 5.0 | 2.5 | 0.0 |
| | 7.0 | 3.5 | 0.0 | 8.0 | 4.0 | 0.0 |
| | 1.0 | 0.5 | 0.0 | 10.0 | 5.0 | 0.0 |
| Day 2 | 3.0 | 1.5 | 0.0 | 0.0 | 0.0 | 0.0 |
| | 4.0 | 2.0 | 0.0 | 1.0 | 0.5 | 0.0 |
| | 2.0 | 1.0 | 0.0 | 3.0 | 1.5 | 0.0 |
| Day 3 | 2.0 | 1.0 | 0.0 | 0.0 | 0.0 | 0.0 |
| | 3.0 | 1.5 | 0.0 | 0.0 | 0.0 | 0.0 |
| | 2.0 | 1.0 | 0.0 | 1.0 | 0.5 | 0.0 |
| *S. aureus* MR (+) | | | | | | |
| Day 1 | 12.0 | 16.0 | 0.0 | 16.0 | 12.0 | 0.0 |
| | 13.0 | 12.5 | 0.0 | 14.0 | 12.0 | 0.0 |
| | 12.0 | 11.0 | 0.0 | 12.0 | 9.0 | 0.0 |

TABLE 13-continued

| | Day 1 | | | | | |
|---|---|---|---|---|---|---|
| | Substrate 5 | | | Substrate 6 | | |
| | Plate 1 ZOI (mm) | Plate 2 ZOI (mm) | Control Plate | Plate 1 ZOI (mm) | Plate 2 ZOI (mm) | Control Plate |
| Day 2 | 10.0 | 14.0 | 0.0 | 10.0 | 9.0 | 0.0 |
| | 9.0 | 10.0 | 0.0 | 9.0 | 10.0 | 0.0 |
| | 11.0 | 10.0 | 0.0 | 9.0 | 5.0 | 0.0 |
| Day 3 | 3.0 | 6.0 | 0.0 | 5.0 | 7.5 | 0.0 |
| | 6.0 | 6.5 | 0.0 | 4.0 | 8.0 | 0.0 |
| | 5.0 | 5.0 | 0.0 | 3.0 | 0.0 | 0.0 |

While the present invention has been described with references to specific embodiments thereof, it should be understood by those skilled in the art that various changes and modifications may be made and equivalents may be substituted without departing from the true spirit and scope of the invention, in particular, it will be understood that the chemical and pharmaceutical details of every design may be slightly different or modified by one of ordinary skill in the art without departing from the scope of the invention. All such modifications are intended to be within the scope of the appended claims.

What is claimed is:

1. A cathodic arc ion plasma deposition method for producing an anti-microbial coating on a substrate, comprising:
    positioning a substrate between an anode and a cathode target, said target comprising an ionizable metal selected from silver, copper, hafnium or zirconium;
    introducing only oxygen gas into a vacuum chamber pressurized to about 0.1 to about 30 mTorr which houses the cathode target and the substrate;
    variably controlling power to the arc to produce a discharge between the anode and the cathode target; and
    moving the substrate toward or away from the target during arc discharge to deposit a high density, adherent anti-microbial macroparticulate metal/metal oxide coating comprising a range of macroparticle sizes of about 1 nm to 50 microns wherein macroparticle size increases with coating thickness to provide a coating that exhibits anti-microbial activity at least four days longer than a uniform coating containing few macroparticles produced without movement of the substrate during deposition under the same deposition conditions.

2. The method of claim 1 wherein power to the arc is externally controlled by a single variable power supply or by at least two independently variable power supplies attached in opposed positions to the cathode target.

3. The method of claim 2 wherein power to the arc is adjusted to about 12 to about 60 volts providing between 5 and about 500 amps during deposition of a 100-200 nm coating on the substrate.

4. The method of claim 1 wherein the substrate comprises a metal.

5. The method of claim 4 wherein the substrate is selected from the group consisting of titanium, steel, chromium, zirconium, nickel, alloys and combinations thereof.

6. The method of claim 1 wherein the substrate comprises a polymer or ceramic.

7. The method of claim 6 wherein the polymer is polypropylene, polyurethane, EPTFE, PTFE, polyimide, polyester, PEEK, UHMWPE, nylon or combinations thereof.

8. The method of claim 7 wherein the polymer is PEEK or polyethylene.

9. The cathodic arc ion plasma deposition method of claim 1 further comprising monitoring the ratio of the metal/metal oxide deposited in the coating in relation to the distance of the substrate from the target, wherein increased antimicrobial activity of the coating correlates with a decrease in said metal/metal oxide ratio.

10. The method of claim 9 further comprising increasing deposition time to obtain a coating thickness of about 50 nm to about 5 microns.

11. The method of claim 1 wherein the deposition is conducted at a temperature between about 25° C. and 75° C.

* * * * *

UNITED STATES PATENT AND TRADEMARK OFFICE
CERTIFICATE OF CORRECTION

| | |
|---|---|
| PATENT NO. | : 8,066,854 B2 |
| APPLICATION NO. | : 11/406607 |
| DATED | : November 29, 2011 |
| INVENTOR(S) | : Daniel M. Storey et al. |

It is certified that error appears in the above-identified patent and that said Letters Patent is hereby corrected as shown below:

Column 7,
Line 25, "an "coated candy" like" should read --a "coated candy" like--.

Column 9,
Line 41, "standards (SOURCE?). The" should read --standards. The--.
Line 54, "solver-coated" should read --silver-coated--.

Column 10,
Line 15, "the '5,454,886 patent" should read --the '886 patent--.
Line 25, "using the conditions used were:" should read --using the conditions:--.

Column 11,
Line 13, "Example 1" should read --Example 11--.

Column 12,
Line 23, "as -11.0 mm" should read --as -1.0 mm--.

Column 15,
Line 22, "eight catheter segment" should read --eight implants. The exposed segment--.
Line 23, "Locations the animal's" should read
   --Locations of the implant sites on the animal's--.

Column 17,
Line 45, "of tissuereaction" should read --of tissue reaction--.
Line 58, "evisible vidence" should read --visible evidence--.

Signed and Sealed this
Thirtieth Day of October, 2012

David J. Kappos
*Director of the United States Patent and Trademark Office*